US011419964B2

(12) United States Patent
Irrgang

(10) Patent No.: US 11,419,964 B2
(45) Date of Patent: Aug. 23, 2022

(54) DIALYSIS MACHINE AND METHOD OF OPERATING A DIALYSIS MACHINE

(71) Applicant: FRESENIUS MEDICAL CARE DEUTSCHLAND GMBH, Bad Homburg (DE)

(72) Inventor: Tobias Irrgang, Aubstadt (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 28 days.

(21) Appl. No.: 16/348,392

(22) PCT Filed: Nov. 8, 2017

(86) PCT No.: PCT/EP2017/001303
§ 371 (c)(1),
(2) Date: May 8, 2019

(87) PCT Pub. No.: WO2018/086739
PCT Pub. Date: May 17, 2018

(65) Prior Publication Data
US 2019/0262519 A1    Aug. 29, 2019

(30) Foreign Application Priority Data

Nov. 8, 2016  (DE) ...................... 10 2016 013 316.3

(51) Int. Cl.
*A61M 1/16*    (2006.01)
(52) U.S. Cl.
CPC ........ *A61M 1/1635* (2014.02); *A61M 1/1601* (2014.02); *A61M 1/1656* (2013.01);
(Continued)

(58) Field of Classification Search
CPC .............. A61M 1/1635; A61M 1/1656; A61M 1/1601; A61M 1/1658; A61M 1/1668; A61M 2205/3386
See application file for complete search history.

(56) References Cited

U.S. PATENT DOCUMENTS

| 4,770,769 A | 9/1988 | Schael |
| 2011/0120302 A1* | 5/2011 | Raiford .................. A61M 1/167 95/19 |

(Continued)

FOREIGN PATENT DOCUMENTS

| CN | 103747860 | 4/2014 |
| CN | 104168933 | 11/2014 |

(Continued)

*Primary Examiner* — Bradley R Spies
*Assistant Examiner* — Jeannie McDermott
(74) *Attorney, Agent, or Firm* — Jacobson Holman PLLC

(57) ABSTRACT

The present invention relates to a dialysis machine having an extracorporeal blood system; a dialysis fluid system having a dialyzer; having a control unit, wherein the dialysis machine furthermore comprises a balancing chamber having two balancing chamber halves for a balanced infeed and draining of dialysis fluid to and from the dialyzer, wherein a line is provided through which the dialysis fluid is conducted to the balancing chamber, and wherein a mixing chamber is provided in which the fresh dialysis fluid or a component thereof is located and which is directly or indirectly connected to a de-airing line closable by a valve; wherein the dialysis machine has a control unit that is configured such that the control unit opens and closes the valve once, or a number of times, in the operating state of the special air separation of the dialysis machine when the balancing chamber half of the balancing chamber in fluid communication with the named line is in its high-pressure phase.

7 Claims, 2 Drawing Sheets

Figure 1:
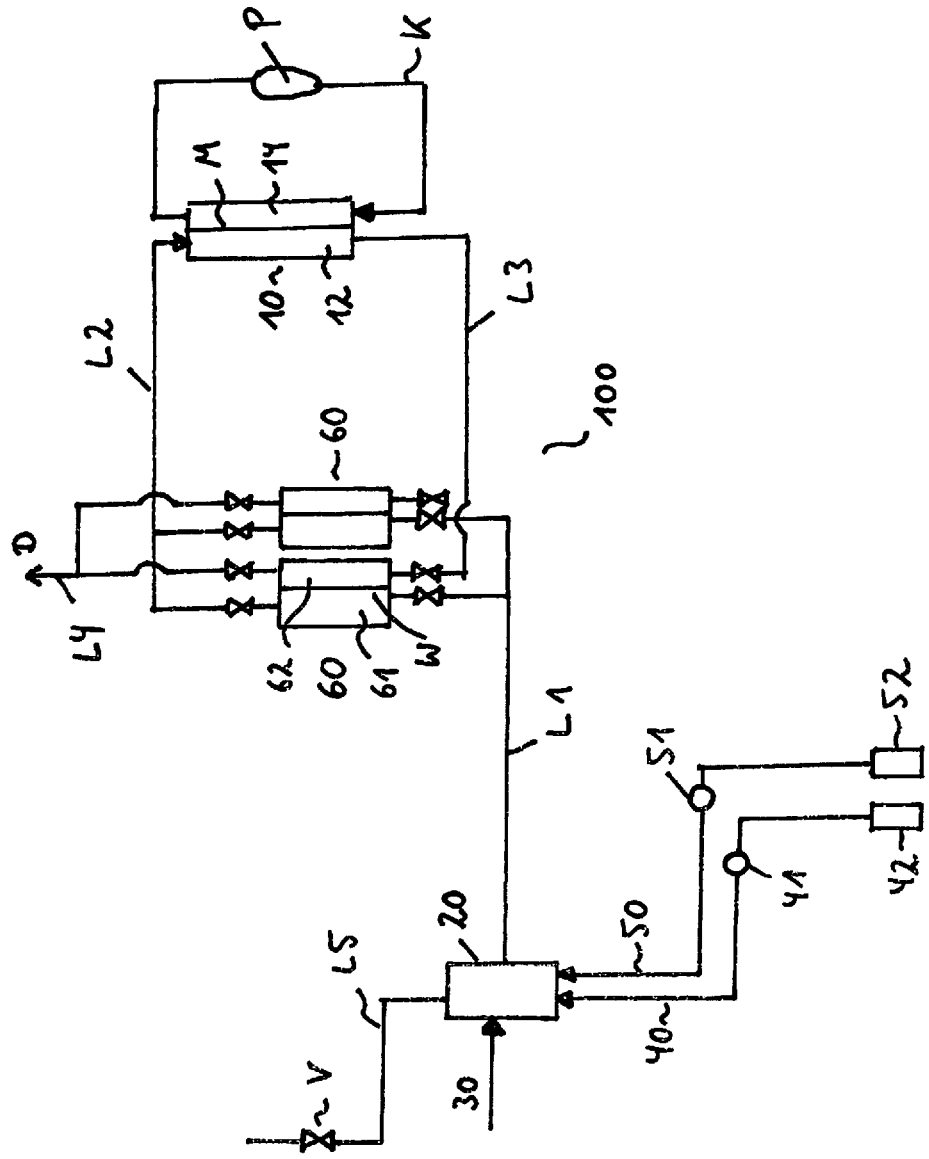

(52) U.S. Cl.
   CPC ......... *A61M 1/1658* (2013.01); *A61M 1/1668* (2014.02); *A61M 2205/3386* (2013.01)

(56) References Cited

U.S. PATENT DOCUMENTS

| | | | |
|---|---|---|---|
| 2011/0120946 A1* | 5/2011 | Levin | A61M 1/1666 210/637 |
| 2012/0265117 A1* | 10/2012 | Fava | A61M 1/3646 604/6.09 |
| 2014/0091022 A1* | 4/2014 | Raiford | A61M 1/1656 210/137 |
| 2014/0209520 A1* | 7/2014 | Koch | B01F 15/0022 210/86 |
| 2016/0058933 A1* | 3/2016 | Ballantyne | A61M 1/1692 210/85 |

FOREIGN PATENT DOCUMENTS

| | | |
|---|---|---|
| CN | 104780955 | 7/2015 |
| CN | 105007958 | 10/2015 |
| DE | 102011106111 | 12/2012 |
| DE | 102015012604 | 3/2017 |
| EP | 0367252 | 5/1990 |
| EP | 0714668 | 6/1996 |
| WO | WO 2012/052151 | 4/2012 |
| WO | WO 2014/012536 | 1/2014 |
| WO | WO 2017/054923 | 4/2017 |

* cited by examiner

DIALYSIS MACHINE AND METHOD OF OPERATING A DIALYSIS MACHINE

The invention relates to a dialysis machine having an extracorporeal blood system, a dialysis fluid system, a dialyzer arranged therein, and a control unit, wherein the dialysis machine furthermore comprises a balancing chamber having two balancing chamber halves for a balanced infeed and draining of dialysis fluid to and from the dialyzer, wherein a line is provided through which the dialysis fluid is conducted to the balancing chamber, and wherein a mixing chamber is provided in which the fresh dialysis fluid or a component thereof is located and which is directly or indirectly connected to a de-airing line closable by a valve.

The invention furthermore relates to a method of operating such a dialysis machine.

Dialysis machines in general are known from the prior art.

Known dialysis machines are used within the course of a dialysis treatment to remove urea and other substances from the blood of a patient having no or reduced renal activity. The central element of a dialysis machine is the dialyzer, with it being a filter unit having a blood chamber and a dialysis fluid chamber which are separated by a semipermeable membrane. The substances to be removed from the blood pass through the semipermeable membrane from the blood chamber into the dialysis fluid chamber in the dialyzer.

A so-called balancing chamber is used for the purpose of balancing the quantity of dialysis fluid fed to the dialyzer and drained therefrom. Said balancing chamber has two balancing chamber halves which are separated from one another by a movable wall, which have an inlet and an outlet and which can be opened and closed via a respective valve. While one of the balancing chamber halves is filled by fresh dialysis fluid, the wall moves away from the filling balancing chamber half and in this manner displaces the consumed dialysis fluid located in the other balancing chamber half. Since both balancing chamber halves are located in the same balancing chamber having fixed walls, the fed volume of fresh dialysis fluid corresponds to the drained volume of consumed dialysis fluid.

It is furthermore known from the prior art to prepare the dialysis fluid at the device itself by the use of concentrate containers whose concentrates are mixed with RO water. In this respect, two concentrate containers are typically used of which one contains a base concentrate and the other an acid concentrate. The concentrates are conveyed by means of concentrate pumps into a mixing chamber in which they are mixed with RO water. This mixture is then conveyed to the balancing chamber and is conducted from there to the dialyzer.

Such a dialysis machine know from the prior art is shown in greatly simplified form in FIG. 1. The patient P is connected via the extracorporeal circuit K to the dialyzer 10 that has a blood-side compartment 14 and a dialysate-side compartment 12 which are separated from one another by a semipermeable membrane M. The blood of the patient is conducted in counter flow to the dialysis fluid through the dialyzer 10 as is indicated by arrows that reproduce the flow direction.

The hydraulic system of the dialysis machine, i.e. the dialysis fluid system, is generally designated by the reference numeral 100.

The dialysis fluid is prepared in the mixing chamber 20 from the fluid, preferably RO water (RO=reverse osmosis), flowing in through the line 30 and from the two concentrates that flow into the mixing chamber 20 through the lines 40, 50. The conveying of the concentrates takes place by means of the pumps 41, 51 that convey the concentrate from the concentrate containers 42, 52.

The line L5 arranged at the mixing chamber 20 serves the de-airing of the dialysis fluid and is closable by the valve V.

The balancing chamber 60 has the above-named balancing chamber halves 61 and 62 that are separated by the movable wall W that is not permeable for dialysis fluid.

To ensure a continuous flow, two balancing chambers 60 are provided such as can be seen from FIG. 1. They can have an identical structure.

The balancing chambers are shown simplified in that their inner walls are preferably shaped such that the wall W can lie completely at them in its extreme positions.

As can furthermore be seen from FIG. 1, each balancing chamber half 61, 62 of a balancing chamber 60 has a valve at the inlet side and at the outlet side to control the inflow and outflow into and out of the balancing chamber halves.

The two balancing chamber halves 61 of the balancing chambers' 60 shown at the left serve the reception of fresh dialysis fluid from the line L1. The dialysis fluid moves from the balancing chamber halves 61 via the line L2 into the dialyzate-side compartment 12 of the dialyzer 10.

The two balancing chamber halves 62 of the balancing chamber 60 shown at the right serve the reception of consumed dialysis fluid that moves via the line L3 from the dialyzer 10 to the balancing chamber halves 62 and that is led after the balancing chamber via the line L4 to a drain (D).

In those cases in which there are no air separators in the concentrate lines 40, 50, the case can occur that air moves into the balancing chamber, which results in a balancing error since the balancing chamber half of the balancing chamber is then not completely filled with fresh dialysis fluid and thus less fresh dialysis liquid is conveyed to the dialyzer than assumed.

The ingress of air into the balancing chamber or into the concentrate lines can take place, for example, when one or both of the concentrate containers is/are empty. In these cases, air is conveyed or entrained via the concentrate lines into the mixing chamber and from there into the balancing chamber.

This entrainment of air takes place by the opening of the de-airing valve V at the dead time of the balancing chamber. The dead time of the balancing chamber is to be understood as the time period in which the wall W is located in an extreme position (deflection fully to the right or to the left) and all the valves of the balancing chamber are closed. This state can, for example, last 100 ms.

Figure 2:
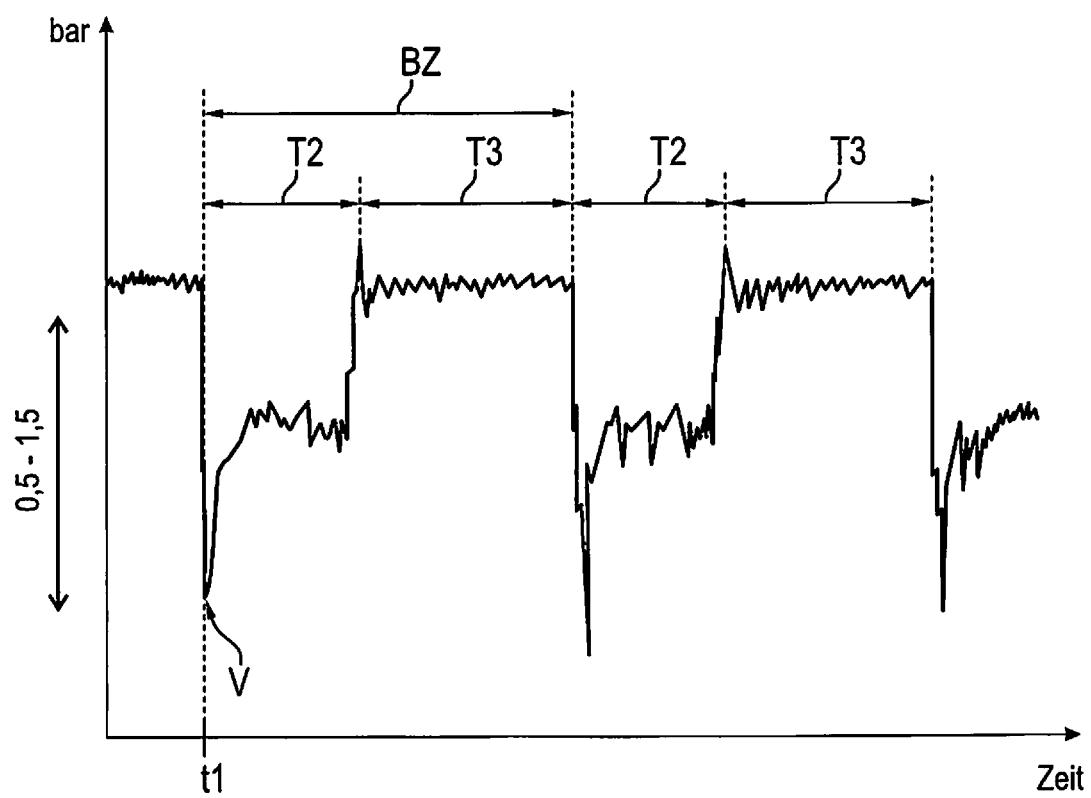

FIG. 2 shows the pressure development over time during a balancing chamber cycle, with the time t1 marking the named dead time. As marked by an arrow V in FIG. 2, the valve V is briefly opened at this time t1. The valve V is subsequently closed and the inflow valve of the balancing chamber is opened so that the pressure in the filling balancing chamber half 61 increases. This filling phase is marked by T2 in FIG. 2. In the subsequent state T3, the balancing chamber half is completely filled, which is also called the high-pressure phase of the balancing chamber.

The reference symbol BZ designates the total balancing chamber half cycle that covers all these phases or times.

The air rises upward in the lines 40. 50 with an open valve V1 and is then entrained into the balancing chamber or balancing chamber half 61 by the filling flow by means of which the balancing chamber 61 is filled. This produces an incorrect balance.

As stated above, the opening of the valve V can result in a collection of air in the balancing chamber, which is unwanted since then no correct fluid volumes are conveyed.

It is therefore the underlying object of the invention to further develop a dialysis machine in accordance with the following disclosure such that an air entry into the balancing chamber is prevented or at least considerably reduced with respect to known devices.

This object is achieved by a dialysis machine having the features described below and by a method of operating a dialysis machine having the features described below.

Provision is accordingly made that the dialysis machine has a control unit that is configured such that the control unit opens and closes the valve once, or preferably a number of times, in the operating state of the special air separation of the dialysis machine when the balancing chamber half of the balancing chamber in fluid communication with the named line (line L1) is in its high-pressure phase.

During this procedure, which is also called the "special air separation" within the framework of the present invention, the respective balancing chamber half is filled and the valve is preferably opened and closed a plurality of times. Since a flow in the direction of the balancing chamber no longer takes place due to the full balancing chamber half, no air is entrained in this process.

The air is expelled mechanically by the opening and closing of the valve preferably taking place a plurality of times, for example, three times, such that less residual air remains in the mixing chamber that could be entrained in the next filling of the balancing chamber.

The probability for the introduction of air into the balancing chamber is substantially reduced overall in this manner.

If this special air separation is again followed by a normal air separation, such as is shown in FIG. 2, no air or a great deal less air is entrained on the opening of the valve V than is the case in the prior art because no air or only very little air is still located in the balancing chamber.

The mixing chamber is preferably connected to one or more concentrate lines through which concentrates move out of concentrate containers into the mixing chamber. These concentrates can, for example, be one acid concentrate and one base concentrate.

The mixing chamber is typically connected to a fresh water connection, in particular to an RO water connection, such that the concentrate or concentrates can be diluted to the desired level.

In a preferred embodiment of the invention, the dialysis machine has recognition means that are configured to detect the lack or an empty state of a concentrate tank and that are connected to the control unit such that it initiates the operating state of the special air separation when the named detection by the recognition means has taken place.

If the recognition means, for example, detect an empty state of a concentrate container, which is not only to be understood such that the container is completely empty, but rather also the state that the filling level is below a specific level, it is assumed that a comparatively large amount of air is present in the mixing chamber or in the lines connected thereto such that the operating mode of the special air separation is initiated in which the valve is opened and closed at least once, preferably a plurality of times, during the high-pressure phase of the balancing chamber or of the balancing chamber half.

The control unit can be configured such that it carries out a normal air separation cycle when neither the lack nor the empty state of a concentrate container is detected on the part of the recognition means, wherein the normal air separation cycle comprises an opening of the valve in the dead time of the balancing chamber, as can be seen from FIG. 2. In this state, no openings and closings of the valve preferably take place in a time following the dead time, in particular not in the high-pressure phase.

The normal air separation mode is typically the normal state, while the special air separation mode is only selected when the lack or the empty state of a concentrate container is recognized.

The present invention is preferably used in dialysis machines that do not have an air separation apparatus.

The present invention furthermore relates to a method of operating a dialysis machine in accordance with the instant disclosure, wherein the valve is opened once or a plurality of times in the operating state of the special air separation of the dialysis machine when the balancing chamber half of the balancing chamber in fluid communication with the line is in its high-pressure state.

As stated above, the operating state of the special air separation is preferably set when a concentrate container is missing or is empty or when other reasons are present during which it is to be anticipated that there is a comparatively large amount of air in the mixing chamber.

Provision is furthermore preferably made that the operating state of the special air separation is not selected when no concentrate container is missing or is empty, but that in this case a normal air separation is carried out that only provides for an opening of the valve in the dead time of the balancing chamber.

Figure 3:
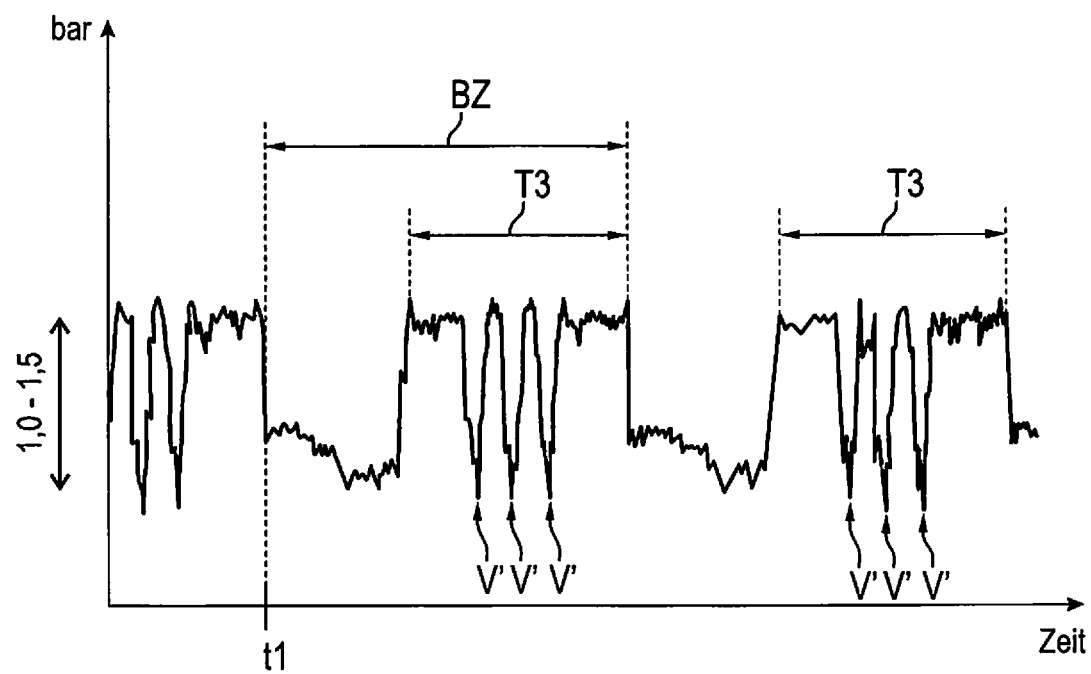

Further details and advantages of the invention result from the embodiments represented in the following with reference to the Figures. There are shown in the Figures:

FIG. 1: a simplified schematic representation of the hydraulic circuit and blood circuit of a dialysis machine;

FIG. 2: the course of the pressure over time with a normal air separation; and FIG. 3: the course of the pressure over the time with a special air separation.

FIG. 1 shows a hydraulic circuit and also the extracorporeal blood circuit of a dialysis machine known from the prior art. This structure can also be present identically or in a modified form in a dialysis machine in accordance with the invention so that the above statements also apply to the present invention.

Within the framework of normal operation, the normal air separations is carried out, such as is described above and is shown in FIG. 2. The air separation takes place by opening the valve V, and indeed at the dead time of the balancing chamber or of the balancing chamber half filled with fresh dialysis fluid, and subsequently no longer during the balancing chamber cycle BZ.

If, however, it is recognized by suitable recognition means such as sensors that excessive air entry is taking place, which can e.g. be caused by the lack of a concentrate container 42, 52 or by its empty state or by an excessively large air content in the mixing chamber or in one of the lines, this is reported to a control unit, not shown, that thereupon initiates the special air separation.

This is characterized in that the valve V in accordance with FIG. 1 is opened once or preferably a plurality of times, e.g. three times, in the high-pressure phase of the balancing chamber half filled with fresh dialysis fluid.

In the high-pressure phase of the balancing chamber half, the latter is completely filled with liquid. This has the consequence that the opening of the valve V does not result in a flow of fluid enriched with air into the balance chamber.

Air is rather removed from the mixing chamber 20 by the opening and closing of the valve so that no air or only a little air enters into the balancing chamber on the switching back into the normal operating mode or into the normal air separating mode. The probability for the occurrence of incorrect balances can thereby be avoided or at least reduced.

FIG. 3 shows the course of the pressure over time in an arrangement in accordance with FIG. 2, wherein the same times and the same time periods are provided with the same reference symbols and it is illustrated that the valve V is opened and closed three times in the high-pressure phase T2, which is designated by the reference symbol V' and makes itself noticeable by corresponding pressure fluctuations. An opening and closing of the valve V preferably does not take place at the dead time t1.

The pressure values indicated in FIGS. 2 and 3 are of an exemplary nature and are not restrictive.

It is finally pointed out that the use of the term "a" or "one" admittedly, but not necessarily means that exactly one of the elements in question is provided, but rather also includes the plurality of elements. It must equally be pointed out that the use of the plural generally also includes one of the elements in question.

The invention claimed is:

1. A dialysis machine having an extracorporeal blood system; a dialysis fluid system having a dialyzer; having a control unit, wherein the dialysis machine furthermore comprises a balancing chamber having two balancing chamber halves for a balanced infeed and draining of dialysis fluid to and from the dialyzer, wherein a line is provided through which the dialysis fluid is conducted to the balancing chamber, and wherein a mixing chamber upstream of the balancing chamber is provided in which the fresh dialysis fluid or a component thereof is located and which is directly or indirectly connected to a de-airing line closable by a valve, wherein the dialysis machine has a control unit that is configured such that the control unit opens and closes the valve once, or a number of times, in the operating state of the special air separation of the dialysis machine when the balancing chamber half of the balancing chamber in fluid communication with the named line is in its high-pressure phase, wherein recognition means are present that are configured to detect each of the lack of a concentrate container, and an empty state of a concentrate container, and when the concentrate container has fallen below a specific filling level and that are connected to the control unit such that the latter initiates the operating state of the special air separation when the named detection has taken place by the recognition means, and wherein the control unit is further configured such that the control unit carries out a normal air separation cycle when neither the lack nor an empty state of a concentrate container nor when the concentrate container has fallen below a certain level is detected on the part of the recognition means, wherein the normal air separation cycle only comprises an opening of the valve in the dead time of the balancing chamber.

2. A dialysis machine in accordance with claim 1, wherein the mixing chamber is connected to concentrate lines through which concentrates move out of concentrate containers into the mixing chamber.

3. A dialysis machine in accordance with claim 1, wherein the mixing chamber is connected to a fresh water connection.

4. A method of operating a dialysis machine in accordance with claim 1, wherein the valve is opened and closed once or a plurality of times in the operating state of the special air separation of the dialysis machine when the balancing chamber half of the balancing chamber in fluid communication with the line is in its high-pressure state.

5. A method in accordance with claim 4, wherein the operating state of the special air separation is selected when a concentrate container is missing or is empty.

6. A method in accordance with claim 4, wherein the operating state of the special air separation is not selected when no concentrate container is missing or is empty.

7. A dialysis machine in accordance with claim 1, wherein the mixing chamber is connected to an RO water connection.

* * * * *